US012159697B2

(12) United States Patent
Bazargan et al.

(10) Patent No.: US 12,159,697 B2
(45) Date of Patent: Dec. 3, 2024

(54) AUTOMATIC NETWORK CONFIGURATION BASED ON BIOMETRIC AUTHENTICATION

(71) Applicant: Medtronic MiniMed, Inc., Northridge, CA (US)

(72) Inventors: Afshin Bazargan, Simi Valley, CA (US); Patrick E. Weydt, Moorpark, CA (US); Hans K. Wenstad, Santa Clarita, CA (US); Adam S. Trock, Simi Valley, CA (US); Seung C. Shin, Los Angeles, CA (US); Samuel Finney, Los Angeles, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 320 days.

(21) Appl. No.: 17/345,538

(22) Filed: Jun. 11, 2021

(65) Prior Publication Data
US 2021/0409943 A1 Dec. 30, 2021

Related U.S. Application Data

(60) Provisional application No. 63/044,993, filed on Jun. 26, 2020.

(51) Int. Cl.
*H04W 12/30* (2021.01)
*A61M 5/142* (2006.01)
(Continued)

(52) U.S. Cl.
CPC ........ *G16H 10/60* (2018.01); *A61M 5/14244* (2013.01); *A61M 5/14248* (2013.01);
(Continued)

(58) Field of Classification Search
CPC .... H04W 12/06; H04W 12/30; H04L 63/0861
See application file for complete search history.

(56) References Cited

U.S. PATENT DOCUMENTS 4,562,751 A   1/1986  Nason et al.
4,685,903 A   8/1987  Cable et al.
(Continued)

FOREIGN PATENT DOCUMENTS

CA       2933166 C    10/2020
CN     106470717 A     3/2017
(Continued)

OTHER PUBLICATIONS

"Glucose meter," Wikipedia the free encyclopedia, last edit made on May 31, 2020, retrieved from https://en.wikipedia.org/w/index.php?title=Giucose_meter&oldid=959883605, accessed on Sep. 13, 2021, 12 pp.

(Continued)

*Primary Examiner* — David J Pearson
(74) *Attorney, Agent, or Firm* — Weaver Austin Villeneuve & Sampson LLP

(57) ABSTRACT

Devices, systems, and techniques for automatic network configuration based on biometric authentication are described herein. In one example, one or more processors may obtain first biometric data derived from one or more sensor signals generated by one or more sensors of a first device coupled to a user. The one or more processors may obtain second biometric data derived from one or more sensor signals generated by one or more sensors of a second device. The one or more processors may compare the first biometric data and the second biometric data, determine that the second device is coupled to the user based on the comparison, and establish a communication link with the second device based on the determination that the second device is coupled to the user.

20 Claims, 7 Drawing Sheets

(51) Int. Cl.

| | | |
|---|---|---|
| *A61M 5/172* | (2006.01) | |
| *G16H 10/60* | (2018.01) | |
| *G16H 40/63* | (2018.01) | |
| *H02J 7/00* | (2006.01) | |
| *H02J 7/02* | (2016.01) | |
| *H04L 9/40* | (2022.01) | |
| *H04W 4/80* | (2018.01) | |
| *H04W 12/06* | (2021.01) | |
| *H04W 12/50* | (2021.01) | |
| *H04W 12/69* | (2021.01) | |

(52) U.S. Cl.
CPC ............ *A61M 5/172* (2013.01); *G16H 40/63* (2018.01); *H02J 7/00032* (2020.01); *H02J 7/02* (2013.01); *H04L 63/0861* (2013.01); *H04W 4/80* (2018.02); *H04W 12/06* (2013.01); *H04W 12/30* (2021.01); *H04W 12/50* (2021.01); *H04W 12/69* (2021.01); *A61M 2205/3584* (2013.01); *A61M 2205/52* (2013.01); *A61M 2205/8243* (2013.01)

(56) References Cited

U.S. PATENT DOCUMENTS

| | | | |
|---|---|---|---|
| 5,080,653 | A | 1/1992 | Voss et al. |
| 5,097,122 | A | 3/1992 | Colman et al. |
| 5,505,709 | A | 4/1996 | Funderburk et al. |
| 6,088,608 | A | 7/2000 | Schulman et al. |
| 6,119,028 | A | 9/2000 | Schulman et al. |
| 6,485,465 | B2 | 11/2002 | Moberg et al. |
| 6,488,643 | B1 | 12/2002 | Turney et al. |
| 6,554,798 | B1 | 4/2003 | Mann et al. |
| 6,558,320 | B1 | 5/2003 | Causey, III et al. |
| 6,558,351 | B1 | 5/2003 | Steil et al. |
| 6,589,229 | B1 | 7/2003 | Connelly et al. |
| 6,641,533 | B2 | 11/2003 | Causey, III et al. |
| 6,659,980 | B2 | 12/2003 | Moberg et al. |
| 6,740,072 | B2 | 5/2004 | Starkweather et al. |
| 6,752,787 | B1 | 6/2004 | Causey, III et al. |
| 6,817,990 | B2 | 11/2004 | Yap et al. |
| 6,827,702 | B2 | 12/2004 | Lebel et al. |
| 6,932,584 | B2 | 8/2005 | Gray et al. |
| 7,323,142 | B2 | 1/2008 | Pendo et al. |
| 7,402,153 | B2 | 7/2008 | Steil et al. |
| 7,621,893 | B2 | 11/2009 | Moberg et al. |
| 8,674,288 | B2 | 3/2014 | Hanson et al. |
| 9,526,834 | B2 | 12/2016 | Keenan et al. |
| 10,159,786 | B2 | 12/2018 | Smith |
| 10,238,794 | B2 | 3/2019 | Kamen et al. |
| 11,735,305 | B2 | 8/2023 | Bazargan et al. |
| 11,955,210 | B2 | 4/2024 | Bazargan et al. |
| 2002/0126036 | A1 | 9/2002 | Flaherty et al. |
| 2004/0117062 | A1 | 6/2004 | Bonney et al. |
| 2007/0121230 | A1 | 5/2007 | Klein |
| 2009/0227925 | A1 | 9/2009 | McBean et al. |
| 2011/0218495 | A1* | 9/2011 | Remde .................. G16H 20/17 604/151 |
| 2011/0231204 | A1 | 9/2011 | De La Huerga |
| 2014/0066889 | A1 | 3/2014 | Grosman et al. |
| 2015/0317855 | A1 | 11/2015 | Sezan et al. |
| 2015/0365826 | A1* | 12/2015 | Mancini ................. G16H 40/63 713/155 |
| 2016/0066184 | A1* | 3/2016 | Bhargav-Spantzel ...................... H04L 63/105 726/7 |
| 2016/0088474 | A1* | 3/2016 | Smith ................... H04W 12/06 370/310 |
| 2016/0135245 | A1* | 5/2016 | Singh ..................... G16H 40/67 455/41.2 |
| 2016/0182496 | A1* | 6/2016 | Weast ................. H04L 63/0853 726/3 |
| 2016/0197916 | A1* | 7/2016 | Ravindran ............. H04L 63/10 726/4 |
| 2016/0274162 | A1 | 9/2016 | Freeman et al. |
| 2016/0309286 | A1* | 10/2016 | Son ......................... H04W 4/80 |
| 2018/0317826 | A1 | 11/2018 | Muhsin et al. |
| 2019/0090135 | A1* | 3/2019 | Milevski ............... H04W 76/10 |
| 2019/0108324 | A1* | 4/2019 | Graube ................. H04L 9/3231 |
| 2019/0344090 | A1 | 11/2019 | Sullivan et al. |
| 2020/0253525 | A1 | 8/2020 | Zhang et al. |
| 2020/0306445 | A1* | 10/2020 | Michaud ................ G16H 20/17 |
| 2021/0402089 | A1 | 12/2021 | Bazargan et al. |
| 2021/0407644 | A1 | 12/2021 | Bazargan et al. |
| 2021/0407645 | A1 | 12/2021 | Bazargan et al. |
| 2023/0157545 | A1* | 5/2023 | KoKovidis ........... H04W 12/50 600/301 |
| 2024/0212807 | A1 | 6/2024 | Bazargan et al. |

FOREIGN PATENT DOCUMENTS

| | | |
|---|---|---|
| CN | 113613616 A | 11/2021 |
| CN | 107615396 B | 6/2022 |
| TW | 202108196 A | 3/2021 |
| TW | 202109196 A | 3/2021 |
| WO | 2014/035570 A2 | 3/2014 |
| WO | 2021262474 A1 | 12/2021 |
| WO | 2021262475 A1 | 12/2021 |

OTHER PUBLICATIONS

"Insulin pump," Wikipedia the free encyclopedia, last edit made on Jun. 13, 2020, retrieved from https://en.wikipedia.org/w/index.php?title=Insulin_pump&oldid=962359925, accessed on Sep. 13, 2021, 11 pp.
International Search Report and Written Opinion of International Application No. PCT/US2021/037335, dated Sep. 27, 2021, 14 pp.
U.S. Appl. No. 17/212,956, filed Mar. 25, 2021, naming inventors Bazargan et al.
U.S. Appl. No. 17/212,982, filed Mar. 25, 2021, naming inventors Bazargan et al.
U.S. Appl. No. 17/213,003, filed Mar. 25, 2021, naming inventors Bazargan et al.
U.S. Final office Action dated Jul. 27, 2023 in U.S. Appl. No. 17/212,982.
U.S. Non-Final Office Action dated Aug. 16, 2023, in U.S. Appl. No. 17/213,003.
U.S. Non-Final Office Action dated Feb. 17, 2023, in U.S. Appl. No. 17/212,982.
U.S. Non-Final Office Action dated Sep. 20, 2022, in U.S. Appl. No. 17/212,956.
International Preliminary Report on Patentability dated Jan. 5, 2023 in PCT Application No. PCT/US2021/037332.
International Preliminary Report on Patentability dated Jan. 5, 2023 in PCT Application No. PCT/US2021/037335.
International Search Report and Written Opinion dated Oct. 5, 2021 in PCT Application No. PCT/US2021/037332.
U.S Advisory Action dated Oct. 27, 2023 in U.S. Appl. No. 17/212,982.
U.S. Non-Final Office Action dated Nov. 22, 2023 in U.S. Appl. No. 17/212,982.
U.S. Notice of Allowance dated Apr. 7, 2023 in U.S. Appl. No. 17/212,956.
U.S. Notice of Allowance dated Dec. 5, 2023 in U.S. Appl. No. 17/213,003.
U.S. Notice of Allowance dated Jan. 20, 2023 in U.S. Appl. No. 17/212,956.
U.S. Final Office Action dated Mar. 1, 2024 in U.S. Appl. No. 17/212,982.
U.S. Appl. No. 18/596,386, inventors Bazargan; Afshin, et al., filed Mar. 5, 2024.
U.S. Advisory Action dated May 13, 2024 in U.S. Appl. No. 17/212,982.
U.S. Notice of Allowance dated Jun. 21, 2024 in U.S. Appl. No. 17/212,982.

* cited by examiner

AUTOMATIC NETWORK CONFIGURATION BASED ON BIOMETRIC AUTHENTICATION

This application claims the benefit of U.S. Provisional Application No. 63/044,993, filed Jun. 26, 2020, the entire content of which is hereby incorporated by reference.

This application discloses subject matter that relates to U.S. patent application Ser. No. 17/212,956, filed Mar. 25, 2021, U.S. patent application Ser. No. 17/212,982, filed Mar. 25, 2021, and U.S. patent application Ser. No. 17/213,003, filed Mar. 25, 2021, each of which is incorporated by reference in its entirety herein.

TECHNICAL FIELD

The disclosure relates to network autoconfiguration and, more particularly, to automatic network configuration based on biometric authentication.

BACKGROUND

While they are in service, many devices update the information they store about their users. For example, in the medical device field, therapies are often tailored to the idiosyncrasies of patients. Thus, when devices are rotated out of service, replacement devices may not be configured with updated information.

To address this problem, the replacement devices can be manually configured with the updated information. However, the tedious task of manually configuring replacement devices may result in user frustration and improper configuration.

SUMMARY

Devices, systems, and techniques for network autoconfiguration are described. More specifically, disclosed herein are devices, systems, and techniques for automatic network configuration based on biometric authentication.

In one example, the disclosure describes a method for automatic network configuration based on biometric authentication, the method comprising: obtaining, by one or more processors, first biometric data derived from one or more sensor signals generated by one or more sensors of a first device coupled to a user; obtaining, by the one or more processors, second biometric data derived from one or more sensor signals generated by one or more sensors of a second device; comparing, by the one or more processors, the first biometric data and the second biometric data; determining, by the one or more processors, that the second device is coupled to the user based on the comparison; and establishing, by the one or more processors, a communication link with the second device based on the determination that the second device is coupled to the user.

In another example, the disclosure describes a system for automatic network configuration based on biometric authentication, the system comprising: one or more processors; and one or more processor-readable storage media storing instructions which, when executed by the one or more processors, cause performance of: obtaining first biometric data derived from one or more sensor signals generated by one or more sensors of a first device coupled to a user; obtaining second biometric data derived from one or more sensor signals generated by one or more sensors of a second device; comparing the first biometric data and the second biometric data; determining that the second device is coupled to the user based on the comparison; and establishing a communication link with the second device based on the determination that the second device is coupled to the user.

In yet another example, the disclosure describes one or more non-transitory processor-readable storage media storing instructions which, when executed by one or more processors, cause performance of: obtaining first biometric data derived from one or more sensor signals generated by one or more sensors of a first device coupled to a user; obtaining second biometric data derived from one or more sensor signals generated by one or more sensors of a second device; comparing the first biometric data and the second biometric data; determining that the second device is coupled to the user based on the comparison; and establishing a communication link with the second device based on the determination that the second device is coupled to the user.

The details of one or more aspects of the disclosure are set forth in the accompanying drawings and the description below. Other features, objects, and advantages of this disclosure will be apparent from the description and drawings, and from the claims.

DETAILED DESCRIPTION

Figure 1:
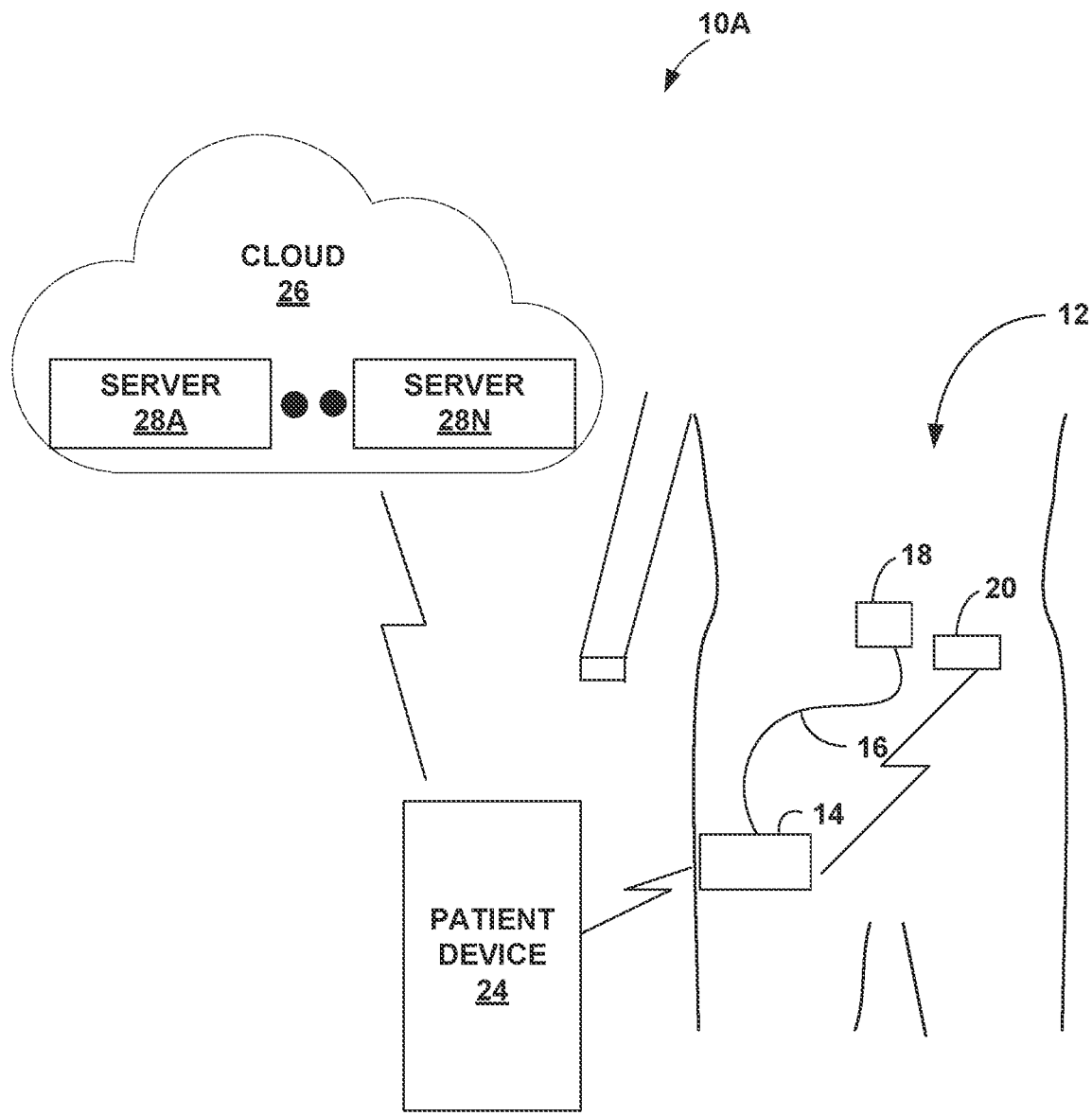
FIG. 1 is a block diagram illustrating an example glucose level management system comprising a tethered pump, in accordance with one or more examples described in this disclosure.

Devices, systems, and techniques for network configuration are described in this disclosure. Although the subject matter of this disclosure is explained using medical devices as examples, it should be appreciated that the subject matter of this disclosure is not limited to medical devices and is equally applicable to any other devices, including wearable devices and other consumer electronic devices. Furthermore, it should be appreciated that the techniques disclosed herein can be practiced with one or more types of insulin (e.g., fast-acting insulin, intermediate-acting insulin, and/or slow-acting insulin). Thus, terms such as "basal insulin" and "bolus insulin" do not necessarily denote different types of insulin. For example, fast-acting insulin may be used for both basal dosages and bolus dosages.

In some examples, a user (e.g., a patient) may employ medical devices (e.g., patch pumps and/or glucose monitoring devices) for glucose level management, and the medical devices may be configured with user-specific configuration data (e.g., configuration data that may be different for different users). Examples of user-specific configuration data include, without limitation, information indicative of any of the following: insulin-on-board, insulin type, a safe basal rate, one or more insulin delivery rate limits, one or more glucose sensor calibration factors, and an insulin sensitivity factor. User-specific configuration data may be stored in volatile memory and/or non-volatile memory. Additionally, user-specific configuration data may be updated while the medical device is in use.

In some examples, the user may possess multiple medical devices of the same type (e.g., having the same manufacturer and model number but different serial numbers). Thus, the user may periodically replace (e.g., swap, cycle, or rotate out) an "in-use" medical device with a replacement medical device of the same type when the in-use medical device approaches an inoperable state (e.g., due to a low battery level, an occluded cannula, and/or an empty insulin reservoir). The term "in-use" should not be considered as limited to a device that is currently in use. For example, in some contexts, the term "in-use" may refer to the device that had been in use until a replacement device was placed into service.

When the user switches from the in-use medical device to the replacement medical device, the replacement medical device may not have the most up-to-date user-specific configuration data. Thus, when the replacement medical device is placed into service, the user typically configures it with the most up-to-date user-specific configuration data. This often involves manually configuring a network connection between the medical devices to facilitate transfer of the configuration data.

However, relying on the user to establish a communication link for updating user-specific configuration data can be burdensome and error-prone. As a result, the communication link may not be established, and the replacement medical device may provide inadequate therapy without the most up-to-date configuration data.

To avoid the aforementioned shortcomings, this disclosure describes example techniques related to automatic network configuration. This can be achieved based on biometric authentication. For instance, upon being placed into service, the replacement medical device (e.g., an insulin delivery device or a continuous glucose monitoring device) may generate biometric data. Examples of biometric data include movement data (e.g., from an inertial measurement sensor such as an accelerometer or a gyroscope), glucose level readings (e.g., from a glucose sensor), skin temperature data (e.g., from a skin temperature sensor), and/or other measurement data obtained from one or more sensors. The replacement medical device may advertise (e.g., based on a short-range wireless transmission capable of being received by any nearby devices) the biometric data, which can be compared with biometric data generated by the in-use medical device to determine whether the in-use medical device and the replacement medical device are/were associated with (e.g., attached to or otherwise worn by) the same patient. If so, a wireless network connection may be automatically established, for example, to transfer patient-specific configuration data from the in-use medical device to the replacement medical device.

FIG. 1 is a block diagram illustrating an example glucose level management system comprising a tethered pump, in accordance with one or more examples described in this disclosure. FIG. 1 illustrates system 10A that includes insulin pump 14, tubing 16, infusion set 18, monitoring device 20 (e.g., a glucose level monitoring device comprising a glucose sensor), patient device 24, and cloud 26. Insulin pump 14 may be described as a tethered pump, because tubing 16 tethers insulin pump 14 to infusion set 18. Cloud 26 represents a local, wide area or global computing network including one or more servers 28A-28N ("one or more servers 28"). Each of one or more servers 28 may include one or more processors and memory. In some examples, the various components may determine changes to therapy based on determination of glucose level for monitoring device 20, and therefore, system 10A may be referred to as glucose level management system 10A.

Patient 12 may be diabetic (e.g., Type 1 diabetic or Type 2 diabetic), and therefore, the glucose level in patient 12 may be controlled with delivery of supplemental insulin. For example, patient 12 may not produce sufficient insulin to control the glucose level or the amount of insulin that patient 12 produces may not be sufficient due to insulin resistance that patient 12 may have developed.

To receive the supplemental insulin, patient 12 may carry insulin pump 14 that couples to tubing 16 for delivery of insulin into patient 12. Infusion set 18 may connect to the skin of patient 12 and include a cannula to deliver insulin into patient 12. Monitoring device 20 may also be coupled to patient 12 to measure glucose level in patient 12. Insulin pump 14, tubing 16, infusion set 18, and monitoring device 20 may together form an insulin pump system. One example of the insulin pump system is the MINIMED™ 670 G insulin pump system by MEDTRONIC MINIMED, INC. However, other examples of insulin pump systems may be used and the example techniques should not be considered limited to the MINIMED™ 670 G insulin pump system. For example, the techniques described in this disclosure may be utilized in insulin pump systems that include wireless communication capabilities. However, the example techniques should not be considered limited to insulin pump systems with wireless communication capabilities, and other types of communication, such as wired communication, may be possible. In another example, insulin pump 14, tubing 16, infusion set 18, and/or monitoring device 20 may be contained in the same housing.

As described in more detail below, in some examples, rather than utilizing a tethered pump system comprising insulin pump 14, tubing 16, infusion set 18, and/or monitoring device 20, patient 12 may utilize a patch pump, such as insulin pump 30 illustrated in FIG. 2. Insulin pump 30 may be described as a patch pump, because it can be removably attached to patient 12 using a small piece of adhesive material worn on the skin. Instead of delivering insulin via tubing and an infusion set, insulin pump 30 may deliver insulin via a cannula extending directly from insulin pump 30. In some examples, a glucose sensor may also be integrated into insulin pump 30. In such examples, insulin pump 30 may be referred to as an all-in-one (AIO) insulin pump.

Referring back to FIG. 1, insulin pump 14 may be a small device that patient 12 can place in different locations. For instance, patient 12 may clip insulin pump 14 to the waistband of pants worn by patient 12. In some examples, to be discreet, patient 12 may place insulin pump 14 in a pocket. In general, insulin pump 14 can be worn in various places, and patient 12 may place insulin pump 14 in a location based on the particular clothes patient 12 is wearing.

To deliver insulin, insulin pump 14 may include one or more reservoirs (e.g., two reservoirs). In some examples, a reservoir may be included in a plastic cartridge that holds up to N units of insulin (e.g., up to 300 units of insulin) and that can be secured within insulin pump 14. In some examples, a reservoir may be integrated into insulin pump 14 such that the reservoir can be filled using a syringe. Insulin pump 14 may be a battery-powered device that is powered by replaceable and/or rechargeable batteries.

Tubing 16 may connect at a first end to a reservoir in insulin pump 14 and may connect at a second end to infusion set 18. Tubing 16 may carry the insulin from the reservoir of insulin pump 14 to patient 12. Tubing 16 may be flexible, allowing for looping or bends to minimize concern of tubing 16 becoming detached from insulin pump 14 or infusion set 18 or concern from tubing 16 breaking.

Infusion set 18 may include a thin cannula that patient 12 inserts into a layer of fat under the skin (e.g., subcutaneous connection). Infusion set 18 may rest near the stomach of patient 12. The insulin may travel from the reservoir of insulin pump 14, through tubing 16, through the cannula in infusion set 18, and into patient 12. In some examples, patient 12 may utilize an infusion set insertion device. Patient 12 may place infusion set 18 into the infusion set insertion device, and with a push of a button on the infusion set insertion device, the infusion set insertion device may insert the cannula of infusion set 18 into the layer of fat of patient 12, and infusion set 18 may rest on top of the skin of the patient with the cannula inserted into the layer of fat of patient 12.

Monitoring device 20 may include a sensor that is inserted under the skin of patient 12, such as near the stomach of patient 12 or in the arm of patient 12 (e.g., subcutaneous connection). The sensor of monitoring device 20 may be configured to measure the interstitial glucose level, which is the glucose found in the fluid between the cells of patient 12. Monitoring device 20 may be configured to continuously or periodically sample the glucose level and rate of change of the glucose level over time.

In one or more examples, insulin pump 14, monitoring device 20, and/or the various components illustrated in FIG. 1, may together form a closed-loop therapy delivery system. For example, patient 12 may set a target glucose level, usually measured in units of milligrams per deciliter, on insulin pump 14. Insulin pump 14 may receive the current glucose level from monitoring device 20 and, in response, may increase or decrease the amount of insulin delivered to patient 12. For example, if the current glucose level is higher than the target glucose level, insulin pump 14 may increase the insulin. If the current glucose level is lower than the target glucose level, insulin pump 14 may temporarily cease delivery of the insulin. Insulin pump 14 may be considered as an example of an automated insulin delivery (AID) device. Other examples of AID devices may be possible, and the techniques described in this disclosure may be applicable to other AID devices. As described in more detail below, insulin pump 14 may be configured to operate in accordance with user-specific configuration data to delivery insulin to patient 12.

Insulin pump 14 and monitoring device 20 may be configured to operate together to mimic some of the ways in which a healthy pancreas works. Insulin pump 14 may be configured to deliver basal dosages, which are small amounts of insulin released throughout the day. There may be times when glucose levels increase, such as due to eating or some other activity that patient 12 undertakes. Insulin pump 14 may be configured to deliver bolus dosages on demand in association with food intake or to correct an undesirably high glucose level in the bloodstream. In one or more examples, if the glucose level rises above a target level, then insulin pump 14 may deliver a bolus dosage to address the increase in glucose level. Insulin pump 14 may be configured to compute basal/bolus dosages and deliver the basal/bolus dosages accordingly. For instance, insulin pump 14 may determine the amount of a basal dosage to deliver and then determine the amount of a bolus dosage to deliver to reduce the glucose level in response to an increase in glucose level due to eating or some other event.

Accordingly, in some examples, monitoring device 20 may sample glucose levels for determining a rate of change in glucose level over time. Monitoring device 20 may output the glucose level to insulin pump 14 (e.g., through a wireless link connection like Bluetooth or BLE). Insulin pump 14 may compare the glucose level to a target glucose level (e.g., as set by patient 12 or a clinician) and adjust the insulin dosage based on the comparison. In some examples, insulin pump 14 may adjust insulin delivery based on a predicted glucose level (e.g., where glucose level is expected to be in the next 30 minutes).

As described above, patient 12 or a clinician may set one or more target glucose levels on insulin pump 14. There may be various ways in which patient 12 or the clinician may set a target glucose level on insulin pump 14. As one example, patient 12 or the clinician may utilize patient device 24 to communicate with insulin pump 14. Examples of patient device 24 include mobile devices, such as smartphones, tablet computers, laptop computers, and the like. In some examples, patient device 24 may be a special programmer or controller (e.g., a dedicated remote control device) for insulin pump 14. Although FIG. 1 illustrates one patient device 24, in some examples, there may be a plurality of patient devices. For instance, system 10A may include a mobile device and a dedicated wireless controller, each of which is an example of patient device 24. For ease of description only, the example techniques are described with respect to patient device 24 with the understanding that patient device 24 may be one or more patient devices.

Patient device 24 may also be configured to interface with monitoring device 20. As one example, patient device 24 may receive information from monitoring device 20 through insulin pump 14, where insulin pump 14 relays the information between patient device 24 and monitoring device 20. As another example, patient device 24 may receive information (e.g., glucose level or rate of change of glucose level) directly from monitoring device 20 (e.g., through a wireless link).

In one or more examples, patient device 24 may comprise a user interface with which patient 12 or the clinician may control insulin pump 14. For example, patient device 24 may comprise a touchscreen that allows patient 12 or the clinician to enter a target glucose level and that outputs the current and/or past glucose level. In some examples, patient device 24 may output notifications to patient 12, such as notifications if the glucose level is too high or too low, as well as notifications regarding any action that patient 12 needs to take. For example, if the batteries of insulin pump 14 are low on charge, then insulin pump 14 may output a low battery indication to patient device 24, and patient device 24 may in turn output a notification to patient 12 to replace or recharge the batteries.

Controlling insulin pump 14 through a touchscreen display device of patient device 24 is merely provided as an example and should not be considered limiting. For example, insulin pump 14 may include pushbuttons that allow patient 12 or the clinician to set the various glucose levels of insulin pump 14. In some examples, insulin pump 14 itself, or in addition to patient device 24, may be configured to output notifications to patient 12. For instance, if the glucose level is too high or too low, insulin pump 14 may output an audible or haptic output. In some examples, if the battery is low, then insulin pump 14 may output a low battery indication on a display of insulin pump 14.

In the example of FIG. 1, insulin pump 14 and/or monitoring device 20 may each correspond to an in-use device or a replacement device. In some examples, the replacement device may be similar, including identical, to the in-use device (e.g., same make and model with same capabilities). However, in some other examples, the replacement device may not be similar (e.g., have different capabilities) to the in-use device.

As described above, during the operation of insulin pump 14 and/or monitoring device 20, user-specific configuration data may be updated. Examples of user-specific configuration data include one or more insulin delivery rate limits (e.g., a maximum basal rate and/or a maximum bolus rate), insulin-on-board (e.g., unmetabolized insulin from one or more previous bolus dosages), a history of insulin delivery, one or more glucose sensor calibration factors (e.g., a previous and/or current sensor sensitivity ratio for converting a sensor signal value into a blood glucose level), a safe basal rate (e.g., a relatively low basal rate that is fixed in that it does not adjust based on current sensor values), and an insulin sensitivity factor (e.g., a ratio that describes the effect of one unit of insulin on glucose levels). It should be appreciated that the above are non-limiting examples of user-specific configuration data stored on insulin pump 14 and that the particular configuration data used may vary from implementation to implementation.

When an in-use device is replaced (e.g., rotated, swapped out, and/or the like), a replacement device may not have the updated user-specific configuration data. However, solutions to address this problem typically rely on human involvement at some level, such as manual configuration of a network connection to facilitate transfer of the configuration data to the replacement device. To eliminate or reduce human involvement, disclosed herein are example techniques for automatically configuring a network connection for providing the updated user-specific configuration data to the replacement device. More specifically, the network connection may be automatically configured upon successfully performing biometric authentication.

Biometric authentication can be performed in a number of ways. For instance, biometric authentication may involve advertisement of biometric data by an in-use device, a replacement device, and/or an intermediate device (e.g., patient device 24). The biometric data may be generated at substantially the same time (e.g., when both in-use and replacement devices are worn by the user) or at different times (e.g., the in-use device may generate biometric data before the replacement device is placed into service, and the replacement device may generate biometric data upon being placed into service). At least one of the devices may compare the biometric data to confirm that the in-use and replacement devices are associated with (e.g., are/were worn by) the same patient.

For example, insulin pump 14 may be an in-use device comprising an accelerometer that generates first biometric data related to patient 12's gait. Insulin pump 14 may store the first biometric data in non-volatile memory for use even after insulin pump 14 is removed from patient 12. A replacement insulin pump may comprise an accelerometer that generates second biometric data related to patient 12's gait. Upon determining that it is being placed into service, the replacement insulin pump may advertise all or part of the second biometric data to nearby devices (including insulin pump 14). Insulin pump 14 may perform a comparison between the advertised biometric data and at least a portion of the first biometric data. Upon determining matching biometric data (e.g., based on determining that the compared biometric data are substantially identical), a network connection may be established (e.g., insulin pump 14 may automatically initiate establishment of the network connection with the replacement insulin pump). Examples of the network connection include a radio frequency (RF) communication link, a BLUETOOTH Low Energy (BLE) communication link, a near-field communication (NFC) link, and an optical communication link.

In some embodiments, insulin pump 14 may also advertise all or part of the first biometric data to nearby devices upon determining that insulin pump 14 is being removed from service. Thus, the replacement insulin pump may perform a comparison between the biometric data advertised by insulin pump 14 and at least a portion of the second biometric data. Based on the comparison, the replacement insulin pump may confirm (e.g., when the compared biometric data are substantially identical) or refuse (e.g., when the compared biometric data are significantly different) the establishment of the network connection with insulin pump 14. For increased security, biometric data advertised by insulin pump 14 may be different from the biometric data advertised by the replacement insulin pump.

In the foregoing example, a network connection is automatically established between an in-use device and a replacement device. Thus, the in-use device may directly communicate (e.g., via push or pull) configuration data to the replacement device over the network connection. However, the techniques disclosed herein are not limited to establishing a network connection between an in-use device and a replacement device. As will be described in greater detail below, in some other examples, a network connection may be automatically established between a replacement device and an intermediate device such that an in-use device may indirectly communicate the configuration data to the replacement device via the intermediate device.

As illustrated in FIG. 1, system 10A includes cloud 26 that includes one or more servers 28. Cloud 26 may include a plurality of network devices (e.g., servers 28), and each network device may include one or more processors. Cloud 26 represents a cloud infrastructure that supports one or more servers 28 which may execute applications or operations requested by one or more users. For example, one or more servers 28 may remotely store, manage, and/or process data that would otherwise be locally stored, managed, and/or processed by patient device 24. One or more processors of one or more servers 28 may share data or resources for performing computations and may be part of computing servers, web servers, database servers, and the like. One or more servers 28 may be within a data center or may be distributed across multiple data centers. In some cases, the data centers may be in different geographical locations.

One or more processors of one or more servers 28, as well as other processing circuitry described herein, can include one or more of any of the following: microprocessors, digital signal processors (DSPs), application specific integrated circuits (ASICs), field programmable gate arrays (FPGAs), or any other equivalent integrated or discrete logic circuitry, as well as any combinations of such components. The functions attributed to the one or more processors, as well as other processing circuitry described herein may be embodied as hardware, firmware, software, or any combination thereof.

One or more processors of one or more servers 28 may be implemented as fixed-function circuits, programmable circuits, or a combination thereof. Fixed-function circuits refer to circuits that provide particular functionality and are preset on the operations that can be performed. Programmable circuits refer to circuits that can be programmed to perform various tasks and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of processors may include distinct circuit blocks (fixed-function or programmable), and in some examples, the one or more processors may include integrated circuits. The one or more processors may include arithmetic logic units (ALUs), elementary function units (EFUs), digital circuits, analog circuits, and/ or programmable cores, formed from programmable circuits. In examples where the operations of one or more servers 28 are performed using software executed by the programmable circuits, memory accessible by one or more servers 28 may store the object code of the software that one or more processors of one or more servers 28 receive and execute.

Figure 2:
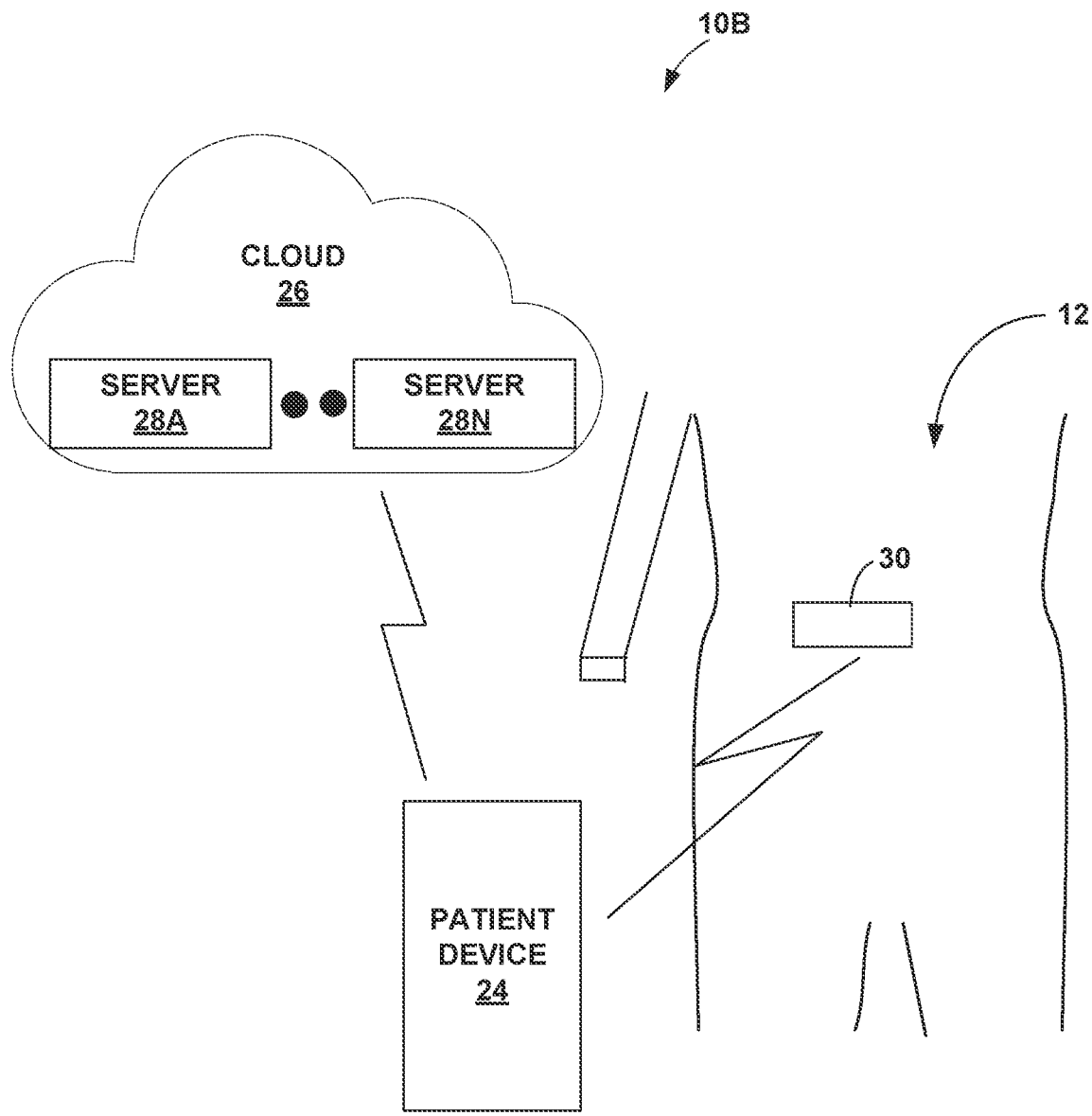
FIG. 2 is a block diagram illustrating an example glucose level management system comprising a patch pump, in accordance with one or more examples described in this disclosure.

FIG. 2 is a block diagram illustrating an example glucose level management system comprising a patch pump, in accordance with one or more examples described in this disclosure. FIG. 2 illustrates system 10B that is similar to system 10A of FIG. 1. However, in system 10B, patient 12 may not have insulin pump 14. Rather, patient 12 may utilize insulin pump 30 to deliver insulin.

Insulin pump 30 may be different than insulin pump 14 in that insulin pump 30 is an example of an on-body-pump. Stated differently, insulin pump 30 is designed to be removably affixed to the skin of patient 12.

In one or more examples, insulin pump 30 may include a glucose sensor similar to that of monitoring device 20. Having the glucose sensor integrated into insulin pump 30 may be beneficial because of reduction in device on-body footprint, more reliable communication between the glucose sensor and components of insulin pump 30 (e.g., having a wired instead of wireless connection between the glucose sensor and the components of insulin pump 30), and sharing of components such as the same processing circuitry for the pump and the glucose sensor, as a few examples. Insulin pump 30 may be referred to as an all-in-one (AIO) insulin pump. In some other examples, rather than the glucose sensor being integrated into insulin pump 30, the glucose sensor may be included in a device (e.g., monitoring device 20) that is separate from insulin pump 30.

Patient 12 may replace insulin pump 30, for example, when the battery of insulin pump 30 is nearly depleted, when the insulin reservoir of insulin pump 30 is empty, or when the cannula of insulin pump 30 becomes occluded. In some examples, patient 12 may replace insulin pump 30 every few days (e.g., every 3 days).

In some examples, insulin pump 30 may be fully disposable in that patient 12 replaces insulin pump 30 in its entirety with a new insulin pump. However, in some other examples, insulin pump 30 may be semi-disposable in that it includes a durable/reusable portion and a consumable/disposable portion.

Figure 3A:
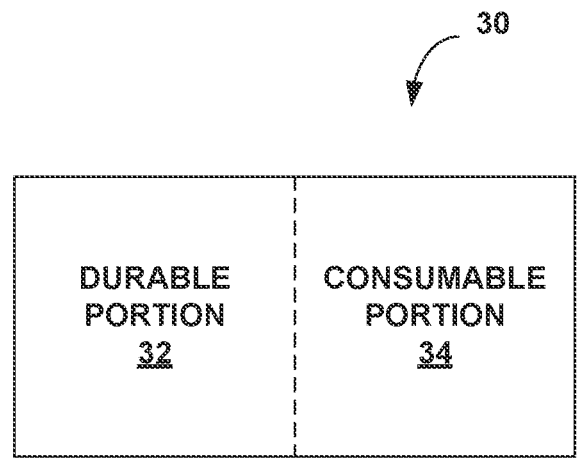
FIGS. 3A and 3B are different perspective views of a semi-disposable patch pump configured to provide therapy, in accordance with one or more examples described in this disclosure.
Figure 3B:
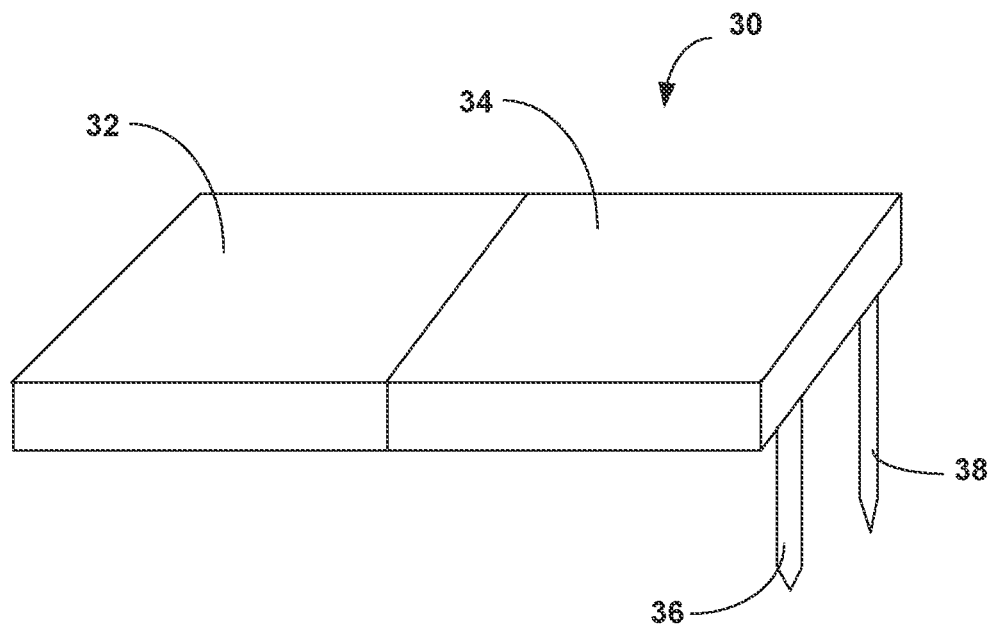

For example, FIGS. 3A and 3B are different perspective views of a semi-disposable patch pump configured to provide therapy, in accordance with one or more examples described in this disclosure. FIG. 3A illustrates durable portion 32 and consumable portion 34 of insulin pump 30. In some examples, durable portion 32 includes electronics (e.g., rechargeable batteries, processor, and memory), and consumable portion 34 includes insulin-contacting components, such as an insulin reservoir. As illustrated in FIG. 3B, consumable portion 34 may also include patient-contacting components, such as cannula 36 and glucose sensor 38. Glucose sensor 38 may be similar to the glucose sensor of monitoring device 20.

There are a variety of ways in which durable portion 32 and consumable portion 34 may be operatively coupled. For example, there may be an electrical connection that facilitates communication between a processor of portion 32 and various components of portion 34, a mechanical connection that enables a motor of portion 32 to exert a force on gears of portion 34, and/or an electromagnetic connection that allows a motor stator in portion 32 to induce movement of a motor rotor in portion 34.

Regardless of whether a patch pump is fully disposable or semi-disposable, it may be replaced periodically. For example, a semi-disposable patch pump may comprise a battery in a durable portion and a reservoir in a consumable portion. When the reservoir is empty, the patch pump may be removed from patient 12, and the durable portion may be separated from the consumable portion. Upon separation, the durable portion may have its battery recharged (e.g., by connecting the durable portion to a charger device), and the consumable portion may simply be discarded. A replacement patch pump may be formed based on removably securing a replacement durable portion (e.g., a second durable portion that has recently been disconnected from the charger device) to a new consumable portion. Thus, patient 12 may have at least two durable portions—an in-use durable portion that is attached to patient 12 and a replacement durable portion that stands by waiting to replace the in-use durable portion.

However, an in-use device and a replacement device may have different data stored in memory. For example, an in-use durable portion may have the most up-to-date configuration data, whereas a replacement durable portion may have default configuration data. To address this problem, this disclosure describes example ways in which to automatically establish a network connection for transferring user-specific configuration data to a replacement device.

Some example ways of automatically establishing a network connection involve a replacement device (e.g., a first medical device) that is configured to automatically determine whether it is being placed into service (e.g., placed in contact with the body of a user). The replacement device may be a replacement for an in-use device (e.g., a second medical device that was previously placed into service to provide medical therapy to patient 12 in accordance with user-specific configuration data stored on the second medical device). Upon determining that it is being placed into service (e.g., based on obtaining biometric data from one or more sensor components), the replacement device may automatically advertise biometric data (e.g., previously and/ or currently obtained biometric data) to nearby devices (e.g., including the in-use device and/or patient device 24) and/or listen for biometric data advertised by another device (e.g., the in-use device and/or patient device 24).

There are a variety of ways in which the replacement device may determine that it is being placed into service. Provided below is a non-exhaustive list of examples that are not necessarily limited to the context of a semi-disposable patch pump.

In some embodiments, the replacement device may determine it is being placed into service based on processing an electrical signal from a skin contact sensor associated with the replacement device. For example, durable portion 32 may include a temperature sensor configured to detect skin temperature indicative of deployment of durable portion 32 on the body of patient 12.

In some embodiments, the replacement device may determine it is being placed into service based on determining that a glucose sensor associated with the replacement device is in contact with interstitial fluid. For example, upon contact with interstitial fluid, a glucose sensor may generate an electrical signal that is communicated to a processor housed in durable portion 32.

In some embodiments, the replacement device may determine it is being placed into service based on accelerometer data indicative of placement on the body of a user. For example, durable portion 32 may include an accelerometer configured to generate signals that can be processed to determine movement that is consistent with walking and/or to synthesize a biometric profile (e.g., based on a user's gait).

For example, insulin pump 30 may be an in-use device comprising one or more sensors that generate first biometric data (e.g., an accelerometer that generates first movement data, a glucose sensor that generates first glucose measurement data, and/or a temperature sensor that generates first skin temperature data). Prior to removing insulin pump 30 from patient 12, a replacement insulin pump may be attached to patient 12. The replacement insulin pump may comprise one or more sensors that generate second biometric data (e.g., an accelerometer that generates second movement data, a glucose sensor that generates second glucose measurement data, and/or a temperature sensor that generates second skin temperature data) at approximately the same time at which the one or more sensors of insulin pump 30 generate the first biometric data. Upon determining that it is being placed into service (e.g., based on generating the second biometric data), the replacement insulin pump may advertise the second biometric data to nearby devices (including insulin pump 30). When insulin pump 30 obtains the second biometric data, insulin pump 30 may compare the first and second biometric data. Upon determining that both the first and second biometric data correspond to patient 12 (e.g., based on determining that all or part of the first and second biometric data are substantially identical), a network connection may be established (e.g., insulin pump 30 may automatically initiate establishment of the network connection with the replacement insulin pump).

Some example ways of automatically establishing a network connection involve an in-use device (e.g., a second medical device) that is configured to automatically determine whether it is being removed from service (e.g., it has been separated from the body of a user or is otherwise approaching an inoperable state). The in-use device may have been previously placed into service to provide medical therapy to patient 12 in accordance with user-specific configuration data stored on the in-use device. Upon determining that it is being removed from service (e.g., based on a failure to further obtain biometric data from one or more sensor components or processing a signal indicative of the in-use device approaching an inoperable state), the in-use device may automatically advertise biometric data (e.g., previously and/or currently obtained biometric data) to nearby devices (e.g., including a replacement device and/or patient device 24) and/or listen for biometric data advertised by a replacement device.

There are various ways in which the in-use device may determine it is being removed from service. For example, in the context of a semi-disposable patch pump, durable portion 32 may determine that it has been separated from consumable portion 34 (e.g., based on a signal/the absence of a signal from a MR sensor, a mechanical switch, a light sensor, and/or a Hall sensor configured to detect a motor rotor in consumable portion 34). Provided below are some other examples that are not necessarily limited to the context of a semi-disposable patch pump.

In some embodiments, the in-use device may determine it is being removed from service based on determining removal of a cannula from the body of a user. For example, cannula removal may cause a decrease in pumping backpressure, which may be detected by a force sensor configured to measure reaction force on a reservoir plunger.

In some embodiments, the in-use device may determine it is being removed from service based on determining the absence of a signal from a skin contact sensor associated with the in-use device. For example, durable portion 32 may include a temperature sensor that fails to detect skin temperature when no longer placed against the body of the user.

In some embodiments, the in-use device may determine it is being removed from service based on determining the absence of a signal from a movement sensor associated with the in-use device. For example, durable portion 32 may include an accelerometer that fails to detect movement when no longer worn by the user.

In some embodiments, the in-use device may determine it is being removed from service based on detecting a reset of a mechanical switch. For example, durable portion 32 may include a mechanical switch configured to automatically reset when no longer in contact with (e.g., separated from) the body of a user.

In some embodiments, the in-use device may determine it is being removed from service based on determining that a glucose sensor associated with the in-use device is no longer in contact with interstitial fluid. For example, a glucose sensor may periodically (e.g., every five minutes) generate an electrical signal when it is in contact with interstitial fluid, so the in-use device may determine that the absence of an expected signal is indicative of removal.

In some embodiments, the in-use device may determine it is being removed from service based on processing a signal indicative of removal of a pull tab situated between the in-use device and a user. For example, a conductive/magnetic pull tab may be adhered to patient 12 such that when in-use device is removed from patient 12, the pull tab breaks a circuit, thereby preventing an electrical signal from being conveyed along the circuit to a processor.

In some embodiments, the in-use device may determine it is being removed from service based on determining that a charger device has been connected to the in-use device. For example, the in-use device may detect power being supplied to its battery.

In some embodiments, the in-use device may determine it is being removed from service based on receiving user input. For example, an in-use device may have one or more buttons which, when pressed by patient 12, causes the in-use device to advertise its biometric data and/or listen for biometric data of a replacement device.

In some embodiments, the in-use device may determine it is being removed from service or is more likely to be removed from service based on detecting that a component has become inoperable. For example, the in-use device may determine that it has a low battery, that it has an empty insulin reservoir, and/or that a glucose sensor has reached the end of its life based on processing a signal from a battery monitor, processing a signal from a force sensor, and/or failing to process any signal from the glucose sensor.

In some embodiments, the in-use device may determine it is being removed from service or is more likely to be removed from service based on discontinuing communications with another device. For example, an in-use device may determine it is being removed from service when it loses a network connection with patient device 24.

For example, insulin pump 30 may be an in-use device comprising one or more sensors that generate first biometric data (e.g., an accelerometer that generates first movement data, a glucose sensor that generates first glucose measurement data, and/or a temperature sensor that generates first skin temperature data). When insulin pump 30 determines it is being removed from service, it may advertise all or part of the first biometric data to nearby devices. At any time relative to advertisement by insulin pump 30 (e.g., prior to, concurrently with, and/or subsequent to), a replacement insulin pump may be placed into service. The replacement insulin pump may comprise one or more sensors that generate second biometric data (e.g., an accelerometer that generates second movement data, a glucose sensor that generates second glucose measurement data, and/or a temperature sensor that generates second skin temperature data). Upon determining that it is being placed into service, the replacement insulin pump may advertise all or part of the second biometric data to nearby devices (including insulin pump 30). For increased security, insulin pump 30 and the replacement insulin pump may advertise different biometric data (e.g., insulin pump 30 may advertise movement data whereas the replacement insulin pump may advertise skin temperature data or insulin pump 30 may advertise glucose measurement data at time T1 whereas the replacement insulin pump may advertise glucose measurement data at time T2).

To perform biometric authentication, insulin pump 30 and the replacement insulin pump may each perform a comparison between biometric data stored in memory and biometric data advertised by the other device. When both insulin pump 30 and the replacement insulin pump determine that the compared biometric data match (e.g., are substantially identical), a network connection may be established between the devices. For instance, insulin pump 30 or the replacement insulin pump (e.g., whichever device makes the earlier determination of matching biometric data) may automatically initiate establishment of the network connection, and the other device may confirm or refuse the establishment of the network connection depending on whether or not it determines matching biometric data.

Some example ways of automatically establishing a network connection involve an intermediate device (e.g., patient device 24) that is configured to store first biometric data obtained from an in-use device. Thus, instead of interacting with the in-use device, a replacement device may interact with the intermediate device to perform biometric authentication.

Figure 4:
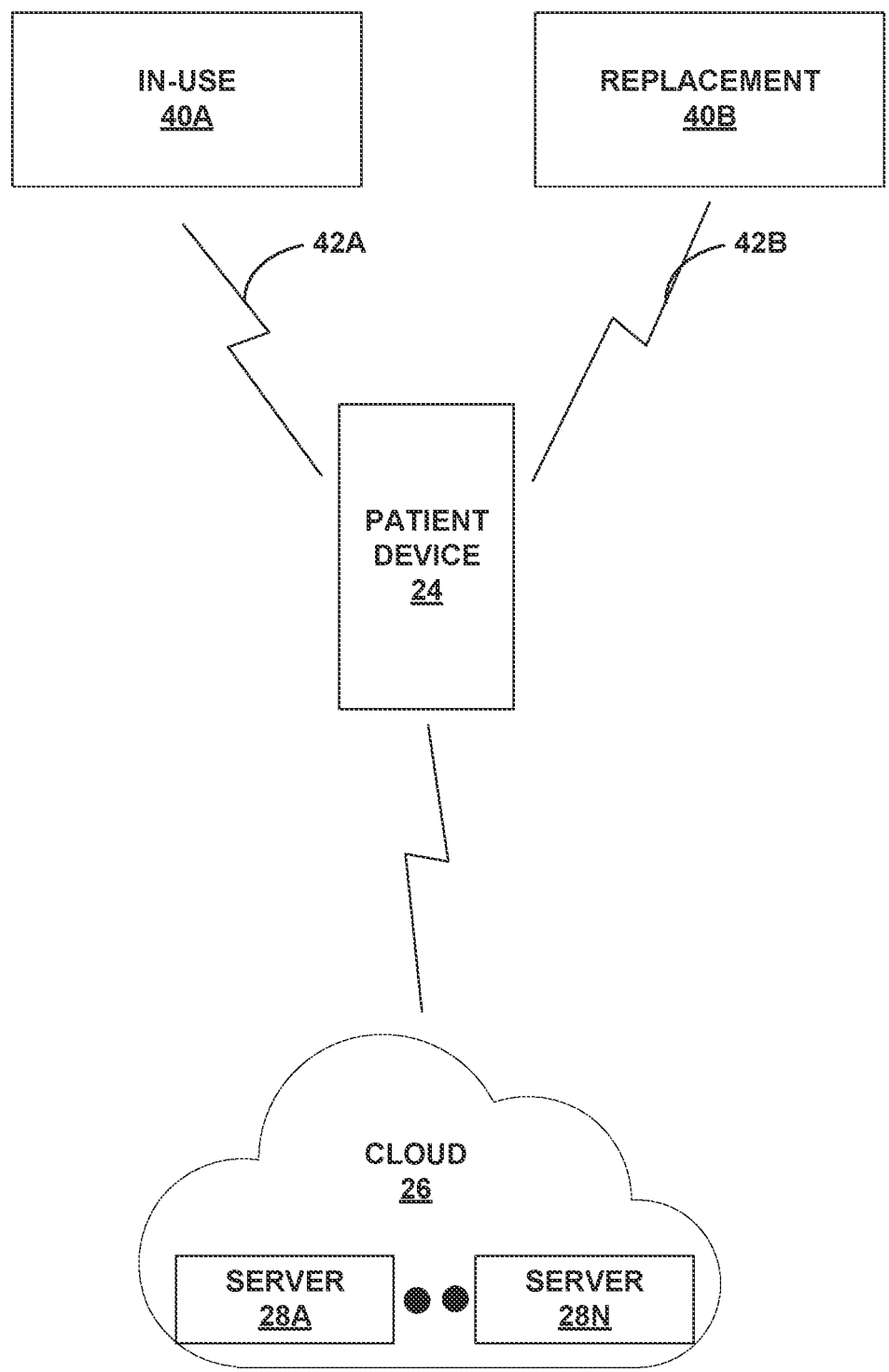
FIG. 4 is a block diagram illustrating an example communication system for transferring user-specific configuration data via an intermediate device, in accordance with one or more examples described in this disclosure.

For example, FIG. 4 is a block diagram illustrating an example communication system for transferring user-specific configuration data via an intermediate device, in accordance with one or more examples described in this disclosure. FIG. 4 illustrates in-use medical device 40A and replacement medical device 40B communicating with patient device 24 via links 42A and 42B, respectively. For ease of explanation, FIG. 4 depicts patient device 24 as concurrently coupled to devices 40A and B. However, in some embodiments, patient device 24 may not be coupled to device 40A when patient device 24 is coupled to device 40B and vice versa. Optionally, patient device 24 may be communicatively coupled to one or more servers 28 of cloud 26.

To establish link 42B, biometric authentication may be performed using patient device 24 and replacement medical device 40B. Patient device 24 may obtain biometric data generated by in-use device 40A. This may be achieved in a variety of ways. For example, device 40A may transmit the biometric data to patient device 24 in response to determining that device 40A is being removed from service and/or whenever biometric data is generated by device 40A. Additionally or alternatively, patient device 24 may periodically poll device 40A to determine whether it has any biometric data to provide, and if so, patient device 24 may request the biometric data.

In some examples, patient device 24 may store the biometric in its memory. For example, patient device 24 may cache the biometric data.

Upon determining that device 40A is being removed from service, patient device 24 may listen for biometric data advertised by device 40B. For example, patient device 24 may determine that device 40A is being removed from service based on obtaining biometric data from device 40A, determining it has lost a network connection with device 40A, and/or receiving user input indicative of device 40A being removed from service. In some embodiments, patient device 24 may advertise all or part of the biometric data obtained from device 40A upon determining that device 40A is being removed from service.

Patient device 24 may otherwise perform operations similar to those ascribed herein to an in-use device. For example, patient device 24 may perform a comparison between biometric data advertised by device 40B and biometric data obtained from device 40A, and upon determining matching biometric data, link 42B may be established (e.g., patient device 24 may automatically initiate or confirm establishment of link 42B).

Figure 5:
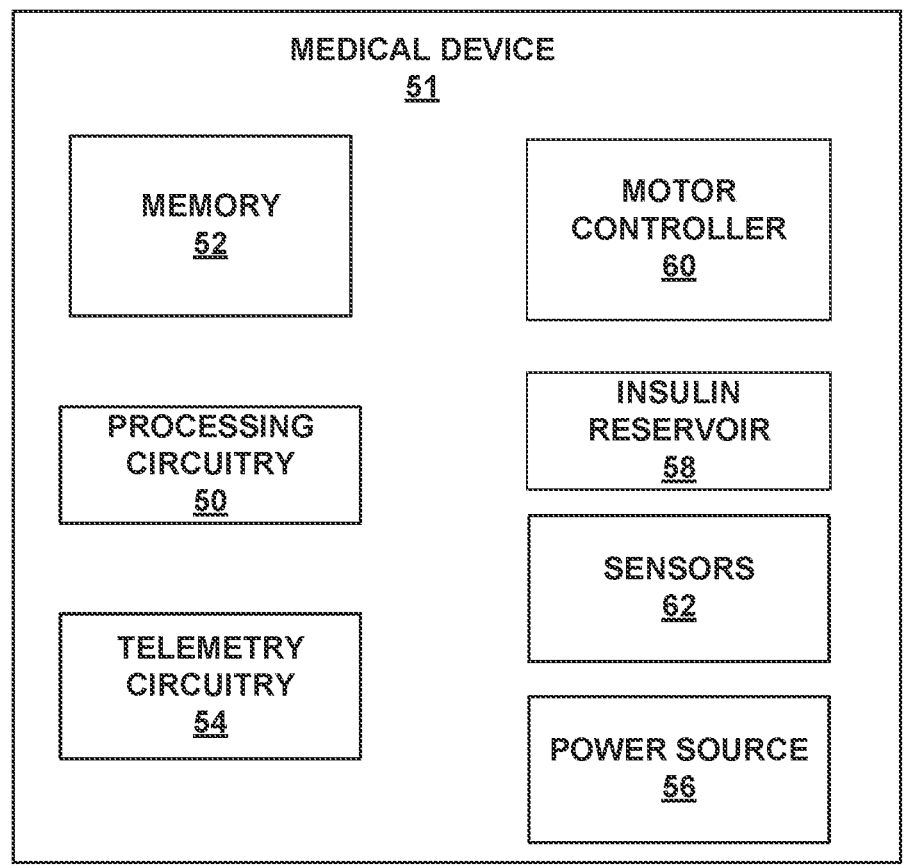
FIG. 5 is a block diagram illustrating an example medical device, in accordance with one or more examples described in this disclosure.

FIG. 5 is a block diagram illustrating an example medical device, in accordance with one or more examples described in this disclosure. FIG. 5 illustrates medical device 51, which may be an in-use device or a replacement device. Examples of medical device 51 include insulin pump 14 and insulin pump 30.

As illustrated, medical device 51 includes processing circuitry 50, memory 52, telemetry circuitry 54, power source 56, insulin reservoir 58, motor controller 60, and one or more sensors 62. Medical device 51 may include more or fewer components than those illustrated in FIG. 5. Also, when medical device 51 is a semi-disposable patch pump, some components of medical device 51 may be located in durable portion 32, and other components may be located in consumable portion 34. For example, processing circuitry 50, memory 52, telemetry circuitry 54, motor controller 60, sensors 62, and power source 56 may be part of durable portion 32; and insulin reservoir 58 may be part of consumable portion 34. However, the particular combination of components in durable portion 32 and consumable portion 34 may vary from implementation to implementation.

Memory 52 may store program instructions that, when executed by processing circuitry 50, cause processing circuitry 50 to provide the functionality ascribed to insulin pump 14, insulin pump 30, device 40A, and/or device 40B throughout this disclosure. Memory 52 may also store biometric data and user-specific configuration data.

Memory 52 may include any volatile, non-volatile, fixed, removable, magnetic, optical, or electrical media, such as RAM, ROM, hard disk, removable magnetic disk, memory cards or sticks, NVRAM, EEPROM, flash memory, and the like. Processing circuitry 50 can take the form one or more microprocessors, DSPs, ASICs, FPGAs, programmable logic circuitry, or the like, and the functions attributed to processing circuitry 50 herein may be embodied as hardware, firmware, software or any combination thereof.

In one or more examples, processing circuitry 50 may utilize the user-specific configuration data stored in memory 52 to output instructions to motor controller 60 for regulating insulin delivery. Motor controller 60 may be configured to control the timing and amount of insulin displacement from insulin reservoir 58 based on the instructions from processing circuitry 50.

One or more sensors 62 may include a glucose sensor (e.g., glucose sensor 38), an inertial measurement sensor, a skin temperature sensor, and/or any other sensors capable of generating signals indicative of medical device 51 being placed into service and/or removed from service. For instance, one or more sensors 62 may include temperature sensors, sweat sensors, resistance sensors, and the like that are configured to generate signals indicative of whether or not medical device 51 is attached to the body of patient 12.

In accordance with one or more examples described in this disclosure, telemetry circuitry 54 may be configured to send and/or receive biometric data and/or user-specific configuration data. Telemetry circuitry 54 may include any suitable hardware, firmware, software, or any combination thereof for enabling communication between medical device 51 and another device (e.g., patient device 24, replacement device 40B, and/or in-use device 40A). Telemetry circuitry 54 may send and/or receive communications with the aid of an antenna, which may be internal and/or external to medical device 51. Telemetry circuitry 54 may be configured to communicate via wired or wireless communication techniques. Examples of local wireless communication techniques that may be employed to facilitate communication include RF communication according to IEEE 802.11, Bluetooth, or BLE specification sets, infrared communication, e.g., according to an IrDA standard, near field communication (NFC), or other standard or proprietary telemetry protocols. Telemetry circuitry 54 may also provide connectivity with a carrier network for access to cloud 26. In this manner, other devices may be capable of communicating with medical device 51.

Power source 56 delivers operating power to the components of medical device 51. In some examples, power source 56 may include a battery, such as a rechargeable or non-rechargeable battery. A non-rechargeable battery may last for several days or possibly longer, while a rechargeable battery may be periodically charged from an external device, e.g., on a daily or weekly basis. Recharging of a rechargeable battery may be accomplished by using an alternating current (AC) outlet or through proximal inductive interaction between charger device 42 and an inductive charging coil within medical device 51. In some examples, the inductive charging coil may be the same as the coil used for communication by telemetry circuitry 54. In some other examples, the inductive charging coil may be separate from the coil used for communication by telemetry circuitry 54.

Figure 6:
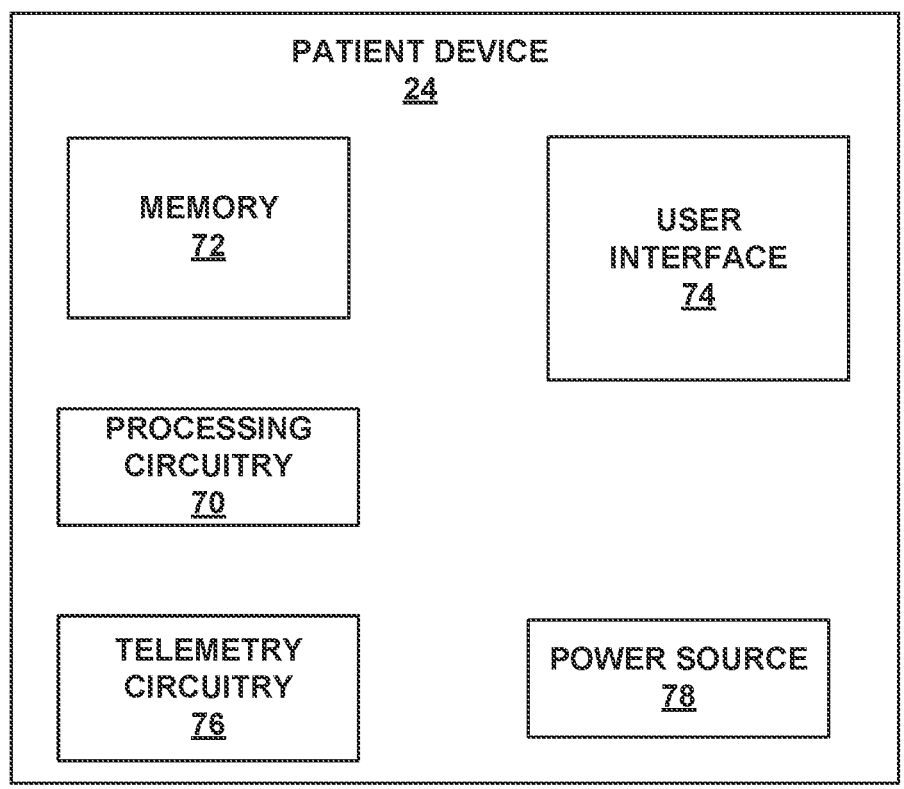
FIG. 6 is a block diagram illustrating an example of a patient device, in accordance with one or more examples described in this disclosure.

FIG. 6 is a block diagram illustrating an example of a patient device, in accordance with one or more examples described in this disclosure. While patient device 24 may generally be described as a hand-held computing device, in some examples, patient device 24 may be a notebook computer, a desktop computer, or a workstation, for example. In some examples, patient device 24 may be a mobile device, such as a smartphone or a tablet computer. Patient device 24 may execute an application that allows patient device 24 to perform example techniques described in this disclosure. In some examples, patient device 24 may be a specialized controller for communicating with medical device 51.

As illustrated in FIG. 6, patient device 24 may include processing circuitry 70, memory 72, user interface 74, telemetry circuitry 76, and power source 78. Memory 72 may store program instructions that, when executed by processing circuitry 70, cause processing circuitry 70 to provide the functionality ascribed to patient device 24 throughout this disclosure.

In some examples, memory 72 of patient device 24 may store biometric data and/or user-specific configuration data. For example, in-use device 40A may transmit the user-specific configuration data to patient device 24, and memory 72 may store the user-specific configuration data for transmission to replacement device 40B or one or more servers 28.

Memory 72 may include any volatile, non-volatile, fixed, removable, magnetic, optical, or electrical media, such as RAM, ROM, hard disk, removable magnetic disk, memory cards or sticks, NVRAM, EEPROM, flash memory, and the like. Processing circuitry 70 can take the form one or more microprocessors, DSPs, ASICs, FPGAs, programmable logic circuitry, or the like, and the functions attributed to processing circuitry 70 herein may be embodied as hardware, firmware, software, or any combination thereof.

User interface 74 may include a button or keypad, lights, a microphone for voice commands, and/or a display device, such as a liquid crystal (LCD). In some examples the display may be a touchscreen. Processing circuitry 70 may present and receive information relating to therapy via user interface 74. For example, processing circuitry 70 may receive user input via user interface 74. The user input may be entered, for example, by pressing a button on a keypad, entering text, or selecting an icon from a touchscreen. For example, to enter initial configuration data for medical device 51, patient 12 or a physician may utilize user interface 74 to enter the configuration data.

Telemetry circuitry 76 may include any suitable hardware, firmware, software, or any combination thereof for enabling communication between patient device 24 and another device, such as one or more servers 28 of cloud 26, in-use device 40A, and replacement device 40B. Telemetry circuitry 76 may send and/or receive communications with the aid of an antenna, which may be internal and/or external to patient device 24. Telemetry circuitry 76 may be configured to communicate via wired or wireless communication techniques. Examples of local wireless communication techniques that may be employed to facilitate communication between patient device 24 and another computing device include RF communication according to IEEE 802.11, Bluetooth, or BLE specification sets, infrared communication, e.g., according to an IrDA standard, near field communication (NFC), or other standard or proprietary telemetry protocols. Telemetry circuitry 76 may also provide connectivity with a carrier network for access to cloud 26. In this manner, other devices may be capable of communicating with patient device 24.

In some examples, telemetry circuitry 76 may include analog or digital RSSI detector circuitry that provides information indicative of the strength of signals received from different devices (e.g., in-use device 40A and replacement device 40B). Processing circuitry 70 may determine which device is in service and which device is out of service based on the information. In some examples, the information may also be indicative of signal quality (e.g., for how long the signal strength is high, how often the signal strength is high, and so forth).

Power source 78 delivers operating power to the components of patient device 24. In some examples, power source 78 may include a battery, such as a rechargeable or non-rechargeable battery. A non-rechargeable battery may last for several months or years, while a rechargeable battery may be periodically charged from an external device, e.g., on a daily or weekly basis. Recharging of a rechargeable battery may be accomplished by using an alternating current (AC) outlet or through proximal inductive interaction between an external charger and an inductive charging coil within patient device 24.

Figure 7:
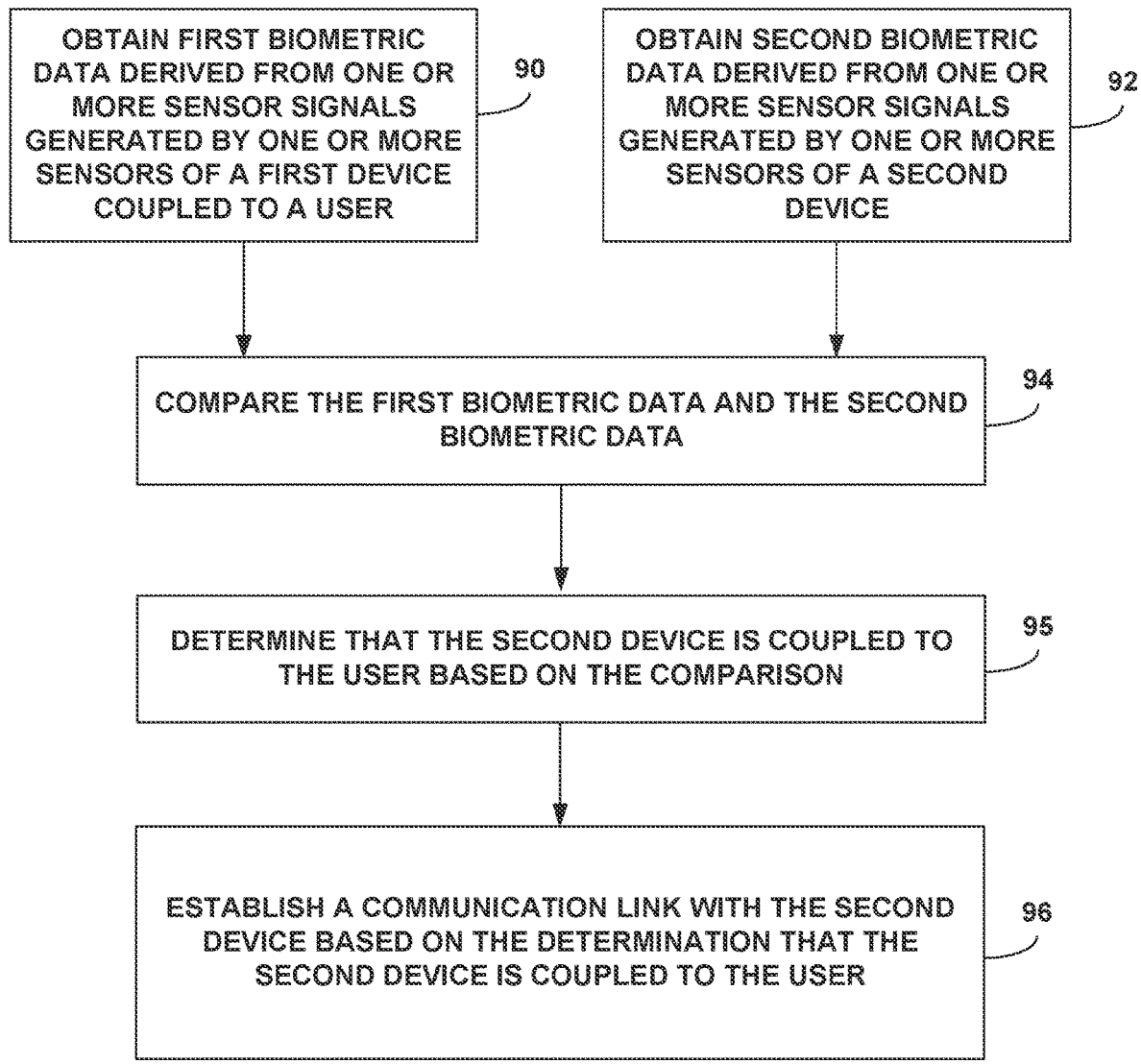
FIG. 7 is a flowchart illustrating an example process for automatic network configuration based on biometric authentication, in accordance with one or more examples described in this disclosure.

FIG. 7 is a flowchart illustrating an example process for automatic network configuration based on biometric authentication, in accordance with one or more examples described in this disclosure. The example process may automatically establish a communication link between a replacement device and either an in-use device or an intermediate device (e.g., patient device 24) logically situated between the replacement device and the in-use device.

As illustrated in FIG. 7, one or more processors (e.g., of the in-use device or the intermediate device) may obtain first biometric data derived from one or more sensor signals generated by one or more sensors of a first device coupled to (e.g., attached to or otherwise worn by) a user (90). The first device may be an in-use medical device (e.g., insulin pump 14, monitoring device 20, or insulin pump 30) that was previously placed into service to provide medical therapy to the user in accordance with user-specific configuration data stored on the in-use medical device. The one or more sensors of the first device may include a temperature sensor, a glucose sensor, and/or an inertial measurement sensor (e.g., an accelerometer or a gyroscope). Thus, examples of the first biometric data may include all or part (e.g., one or more features) of each of the following: skin temperature data, glucose measurement data, and movement data (e.g., acceleration data). For instance, the first biometric data may include all skin temperature data for a predetermined time period; all glucose measurement data for a predetermined time period; all acceleration data for a predetermined time period; absolute or relative timings for a predetermined number of changes in skin temperature; absolute or relative timings for a plurality of glucose level inflection points (e.g., local maxima and/or minima); and/or absolute or relative timings for a plurality of accelerations exceeding a predetermined threshold. In another example, the first biometric data may include each rate of change in the skin temperature data for the predetermined time period; each rate of change in the glucose measurement data for the predetermined time period; each rate of change in the acceleration data for the predetermined time period; an absolute or relative timing for each pre-determined rate of change in skin temperature; an absolute or relative timing for each pre-determined rate of change in glucose level; and an absolute or relative timing for each acceleration exceeding a predetermined threshold.

It should be appreciated that although the one or more sensor signals may be generated when the first device is coupled to the user, the first biometric data may be obtained when the first device is either coupled to or decoupled from the user. For example, the first biometric data may be derived based on processing of the one or more sensor signals after the first device is removed from the user.

At any time relative to obtaining the first biometric data (e.g., prior to, concurrently with, and/or subsequent to), the one or more processors may obtain second biometric data derived from one or more sensor signals generated by one or more sensors of a second device (92). The second device may be a replacement medical device (e.g., a replacement insulin pump or a replacement monitoring device) for the first device. The one or more sensors of the second device may include a temperature sensor, a glucose sensor, and/or an inertial measurement sensor (e.g., an accelerometer or a gyroscope). Thus, examples of the second biometric data may include all or part (e.g., one or more features) of each of the following: skin temperature data, glucose measurement data, and movement data (e.g., acceleration data). For instance, the second biometric data may include all skin temperature data for a predetermined time period (e.g., the same time period to which the skin temperature data of the first biometric data corresponds); all glucose measurement data for a predetermined time period (e.g., the same time period to which the glucose measurement data of the first biometric data corresponds); all acceleration data for a predetermined time period (e.g., the same time period to which the acceleration data of the first biometric data corresponds); absolute or relative timings for a predetermined number of changes in skin temperature; absolute or relative timings for a plurality of glucose level inflection points (e.g., local maxima and/or minima); and/or absolute or relative timings for a plurality of accelerations exceeding a predetermined threshold. In another example, the second biometric data may include each rate of change in the skin temperature data for the predetermined time period; each rate of change in the glucose measurement data for the predetermined time period; each rate of change in the acceleration data for the predetermined time period; an absolute or relative timing for each pre-determined rate of change in skin temperature; an absolute or relative timing for each pre-determined rate of change in glucose level; and an absolute or relative timing for each acceleration exceeding a predetermined threshold. The second biometric data may have been advertised by the second device to any nearby devices (e.g., any devices in a predetermined area local to the second device) when the second device determined (e.g., automatically) that it was being placed into service.

The one or more processors may compare the first biometric data and the second biometric data (94). In some ways, the biometric data are analogous to passkeys that are exchanged during a BLUETOOTH pairing process.

Based on the comparison, the one or more processors may determine whether or not the second device is coupled to the user. More specifically, if the first and second biometric data match, the one or more processors may determine that the second device is coupled to the user (95). If the first device remained coupled during the biometric authentication of the second device, the one or more processors may generate output data instructing the user to remove the first device. However, if the first and second biometric data do not match, the one or more processors may determine that the second device is not coupled to the user (e.g., is coupled to a different user).

Based on the determination that the second device is coupled to the user, the one or more processors may establish a communication link with the second device (96). Establishing the communication link may comprise initiating establishment of the communication link (e.g., transmitting a connection request to the second device). Alternatively, establishing the communication link may comprise confirming establishment of the communication link (e.g., affirmatively responding to a connection request from the second device). Via the above communication link, user-specific configuration data may be communicated to the second device.

It should be appreciated that the process depicted in FIG. 7 is merely provided as an example and that the process may be modified without deviating from the scope of the present disclosure. More specifically, the example process may be practiced in a different order or with more/fewer tasks. For example, prior to establishing the communication link (e.g., concurrently with task 92, task 94, or task 95), the one or more processors may obtain third biometric data derived from the one or more sensor signals generated by the one or more sensors of the first device. For increased security, the third biometric data may be different from the first biometric data (e.g., the first and third biometric data may correspond to different time periods, different features of the one or more sensor signals, and/or different sensors altogether). Furthermore, upon determining (e.g., automatically) that the first device is being removed from service, the one or more processors may advertise the third biometric data to any nearby devices (e.g., any devices in a predetermined area local to the one or more processors).

The following describes some example techniques that may be utilized separately or together in any combination.

Example 1: A method for automatic network configuration based on biometric authentication, the method includes obtaining, by one or more processors, first biometric data derived from one or more sensor signals generated by one or more sensors of a first device coupled to a user; obtaining, by the one or more processors, second biometric data derived from one or more sensor signals generated by one or more sensors of a second device; comparing, by the one or more processors, the first biometric data and the second biometric data; determining, by the one or more processors, that the second device is coupled to the user based on the comparison; and establishing, by the one or more processors, a communication link with the second device based on the determination that the second device is coupled to the user.

Example 2: The method of example 1, further comprising prior to establishing the communication link, obtaining third biometric data derived from the one or more sensor signals generated by the one or more sensors of the first device; and advertising the third biometric data to any devices in a predetermined area local to the one or more processors.

Example 3: The method of any of examples 1 and 2, wherein the third biometric data is different from the first biometric data.

Example 4: The method of any of examples 1 through 3, wherein advertising the third biometric data is performed upon determining that the first device is being removed from service.

Example 5: The method of any of examples 1 through 4, wherein the second biometric data is advertised to any devices in a predetermined area local to the second device when the second device determines it is being placed into service.

Example 6: The method of any of examples 1 through 5, wherein establishing the communication link with the second device comprises initiating establishment of the communication link.

Example 7: The method of any of examples 1 through 6, wherein establishing the communication link with the second device comprises confirming establishment of the communication link.

Example 8: The method of any of examples 1 through 7, further comprising communicating user-specific configuration data to the second device via the communication link.

Example 9: The method of any of examples 1 through 8, wherein the first device comprises the one or more processors.

Example 10: The method of any of examples 1 through 9, wherein an intermediate device is logically situated between the first and second devices, and wherein the intermediate device comprises the one or more processors.

Example 11: The method of any of examples 1 through 10, wherein the first biometric data and the second biometric data correspond to the same time period.

Example 12: The method of any of examples 1 through 11, wherein the one or more sensors of the first device and the one or more sensors of the second device include a temperature sensor.

Example 13: The method of any of examples 1 through 12, wherein the one or more sensors of the first device and the one or more sensors of the second device include a glucose sensor.

Example 14: The method of any of examples 1 through 13, wherein the first biometric data and the second biometric data comprise absolute or relative timings for a plurality of glucose level inflection points.

Example 15: The method of any of examples 1 through 14, wherein the one or more sensors of the first device and the one or more sensors of the second device include an inertial measurement sensor.

Example 16: The method of any of examples 1 through 15, wherein the first biometric data and the second biometric data comprise absolute or relative timings for a plurality of accelerations exceeding a predetermined threshold.

Example 17: The method of any of examples 1 through 16, wherein each of the first device and the second device includes an insulin pump.

Example 18: A system for automatic network configuration based on biometric authentication, the system includes one or more processors; and one or more processor-readable storage media storing instructions which, when executed by the one or more processors, cause performance of: obtaining first biometric data derived from one or more sensor signals generated by one or more sensors of a first device coupled to a user; obtaining second biometric data derived from one or more sensor signals generated by one or more sensors of a second device; comparing the first biometric data and the second biometric data; determining that the second device is coupled to the user based on the comparison; and establishing a communication link with the second device based on the determination that the second device is coupled to the user.

Example 19: The system of claim 18, wherein the one or more processor-readable storage media further store instructions which, when executed by the one or more processors, cause performance of: prior to establishing the communication link, obtaining third biometric data derived from the one or more sensor signals generated by the one or more sensors of the first device; and advertising the third biometric data to any devices in a predetermined area local to the one or more processors.

Example 20: One or more non-transitory processor-readable storage media storing instructions which, when executed by one or more processors, cause performance of obtaining first biometric data derived from one or more sensor signals generated by one or more sensors of a first device coupled to a user; obtaining second biometric data derived from one or more sensor signals generated by one or more sensors of a second device; comparing the first biometric data and the second biometric data; determining that the second device is coupled to the user based on the comparison; and establishing a communication link with the second device based on the determination that the second device is coupled to the user.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including one or more processors of cloud 26, one or more processors of patient device 24, one or more processors of insulin pump 14, or some combination thereof. The one or more processors may be one or more integrated circuits (ICs), and/or discrete electrical circuitry, residing in various locations in the example systems described in this disclosure.

The one or more processors or processing circuitry utilized for example techniques described in this disclosure may be implemented as fixed-function circuits, programmable circuits, or a combination thereof. Fixed-function circuits refer to circuits that provide particular functionality, and are preset on the operations that can be performed. Programmable circuits refer to circuits that can be programmed to perform various tasks, and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits. The processors or processing circuitry may include arithmetic logic units (ALUs), elementary function units (EFUs), digital circuits, analog circuits, and/or programmable cores, formed from programmable circuits. In examples where the operations of the processors or processing circuitry are performed using software executed by the programmable circuits, memory accessible by the processors or processing circuitry may store the object code of the software that the processors or processing circuitry receive and execute.

Various aspects of the disclosure have been described. These and other aspects are within the scope of the following claims.

What is claimed is:

1. A method for automatic network configuration based on biometric authentication, the method comprising:
    obtaining, by one or more processors, first biometric data from a first device that includes one or more sensors and that is entirely attached to a body of a user, wherein the first biometric data is derived from one or more sensor signals generated by the one or more sensors of the first device;
    obtaining, by the one or more processors, second biometric data from a second device that includes one or more sensors and that is entirely attachable to the body of the user, wherein the second biometric data is derived from one or more sensor signals generated by the one or more sensors of the second device;
    comparing, by the one or more processors, the first biometric data and the second biometric data;
    determining, by the one or more processors, that the second device is attached to the body of the user based on the comparison;
    establishing, by the one or more processors, a communication link with the second device based on the determination that the second device is attached to the body of the user; and
    instructing, by the one or more processors, to detach the first device from the body of the user.

2. The method of claim 1, further comprising:
    prior to establishing the communication link, obtaining third biometric data derived from the one or more sensor signals generated by the one or more sensors of the first device; and
    advertising the third biometric data to any devices in a predetermined area local to the one or more processors.

3. The method of claim 2, wherein the third biometric data is different from the first biometric data.

4. The method of claim 2, wherein advertising the third biometric data is performed upon determining that the first device is being removed from service.

5. The method of claim 1, wherein the second biometric data is advertised to any devices in a predetermined area local to the second device when the second device determines it is being placed into service.

6. The method of claim 1, wherein establishing the communication link with the second device comprises initiating establishment of the communication link.

7. The method of claim 1, wherein establishing the communication link with the second device comprises confirming establishment of the communication link.

8. The method of claim 1, further comprising communicating user-specific configuration data to the second device via the communication link.

9. The method of claim 1, wherein the first device comprises the one or more processors.

10. The method of claim 1, wherein an intermediate device is logically situated between the first and second devices, and wherein the intermediate device comprises the one or more processors.

11. The method of claim 1, wherein the first biometric data and the second biometric data correspond to the same time period.

12. The method of claim 1, wherein the one or more sensors of the first device and the one or more sensors of the second device include a temperature sensor.

13. The method of claim 1, wherein the one or more sensors of the first device and the one or more sensors of the second device include a glucose sensor.

14. The method of claim 1, wherein the first biometric data and the second biometric data comprise absolute or relative timings for a plurality of glucose level inflection points.

15. The method of claim 1, wherein the one or more sensors of the first device and the one or more sensors of the second device include an inertial measurement sensor.

16. The method of claim 1, wherein the first biometric data and the second biometric data comprise absolute or relative timings for a plurality of accelerations exceeding a predetermined threshold.

17. The method of claim 1, wherein each of the first device and the second device includes an insulin pump.

18. A system for automatic network configuration based on biometric authentication, the system comprising:
one or more processors; and
one or more processor-readable storage media storing instructions which, when executed by the one or more processors, cause performance of:
obtaining first biometric data from a first device that includes one or more sensors and that is entirely attached to a body of a user, wherein the first biometric data is derived from one or more sensor signals generated by the one or more sensors of the first device;
obtaining second biometric data from a second device that includes one or more sensors and that is entirely attachable to the body of the user, wherein the second biometric data is derived from one or more sensor signals generated by the one or more sensors of the second device;
comparing the first biometric data and the second biometric data;
determining that the second device is attached to the body of the user based on the comparison;
establishing a communication link with the second device based on the determination that the second device is attached to the body of the user; and
instructing, by the one or more processors, to detach the first device from the body of the user.

19. The system of claim 18, wherein the one or more processor-readable storage media further store instructions which, when executed by the one or more processors, cause performance of:
prior to establishing the communication link, obtaining third biometric data derived from the one or more sensor signals generated by the one or more sensors of the first device; and
advertising the third biometric data to any devices in a predetermined area local to the one or more processors.

20. One or more non-transitory processor-readable storage media storing instructions which, when executed by one or more processors, cause performance of:
obtaining first biometric data from a first device that includes one or more sensors and that is entirely attached to a body of a user, wherein the first biometric data is derived from one or more sensor signals generated by the one or more sensors of the first device;
obtaining second biometric data from a second device that includes one or more sensors and that is entirely attachable to the body of the user, wherein the second biometric data is derived from one or more sensor signals generated by the one or more sensors of the second device;
comparing the first biometric data and the second biometric data;
determining that the second device is attached to the body of the user based on the comparison;
establishing a communication link with the second device based on the determination that the second device is attached to the body of the user; and
instructing, by the one or more processors, to detach the first device from the body of the user.

* * * * *